United States Patent [19]

Hester, Jr.

[11] 4,021,441
[45] * May 3, 1977

[54] 1-[(ALLYLAMINO)-METHYL]-6-PHENYL-4H-S-TRIAZOLE [4,3-a][1,4]BENZODIAZEPINES

[75] Inventor: Jackson B. Hester, Jr., Galesburg, Mich.

[73] Assignee: The Upjohn Company, Kalamazoo, Mich.

[*] Notice: The portion of the term of this patent subsequent to July 1, 1992, has been disclaimed.

[22] Filed: Apr. 7, 1975

[21] Appl. No.: 565,710

[52] U.S. Cl. .............................. 260/308 R; 71/92; 424/269
[51] Int. Cl.² .................................. C07D 487/04
[58] Field of Search .............................. 260/308 R

[56] References Cited
UNITED STATES PATENTS

| 3,842,090 | 10/1974 | Gall et al. | 260/308 R |
| 3,870,706 | 3/1975 | Allgeier et al. | 260/308 R |
| 3,892,763 | 7/1975 | Hester | 260/308 R |

FOREIGN PATENTS OR APPLICATIONS 2,118,028  11/1972  France ...................... 260/308 R Primary Examiner—Raymond V. Rush
Attorney, Agent, or Firm—Hans L. Berneis

[57] ABSTRACT

Compounds of the formula II:

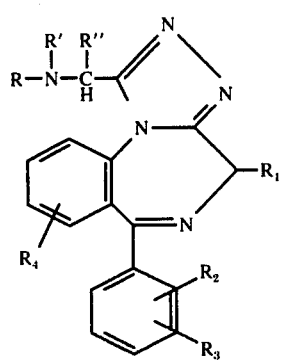

wherein R is cyclopropyl, cyclopropylmethyl, or allyl; wherein R', R'', and $R_1$ are hydrogen or alkyl of 1 to 3 carbon atoms inclusive; and wherein $R_2$, $R_3$, and $R_4$ are hydrogen, alkyl as defined above, fluoro, chloro, bromo, nitro, trifluoromethyl, or alkylthio in which alkyl is defined as above, are prepared by reacting a compound of the formula I.

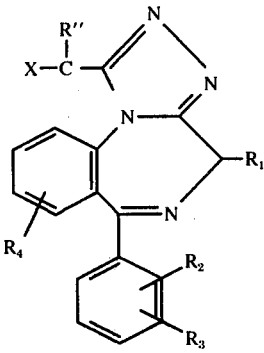

wherein R'', $R_1$, $R_2$, $R_3$, and $R_4$ are defined as above, and wherein X is chlorine or bromine, with an amine of the formula

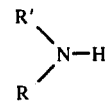

wherein R and R' are defined as above.

The compounds of formula II and the pharmacologically acceptable acid salts thereof have tranquilizing, sedative, antianxiety, and anticonvulsant activity and can be used in animals and birds.

6 Claims, No Drawings

1-[(ALLYLAMINO)-METHYL]-6-PHENYL-4H-S-TRIAZOLE [4,3-a][1,4]BENZODIAZEPINES

BACKGROUND OF THE INVENTION

FIELD OF THE INVENTION

This invention is directed to new organic compounds and is particularly concerned with novel 1-substituted-6-phenyl-4H-s-triazolo[4,3-a][1,4]benzodiazepines of the formula 11 and a process for the production thereof.

The novel compounds and the process of production therefor can be illustratively represented as follows:

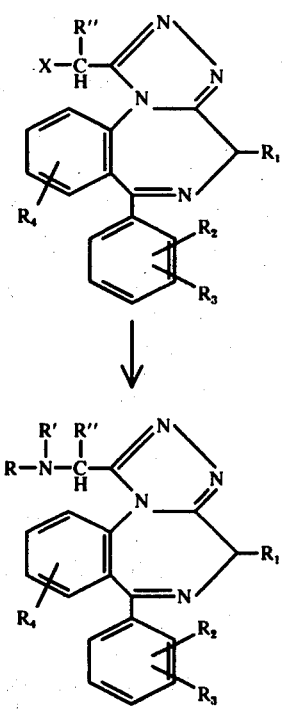

wherein R is cyclopropyl, cyclopropylmethyl, or allyl; wherein R', R'', and $R_1$ are hydrogen or alkyl of 1 or 3 carbon atoms inclusive; and wherein $R_2$, $R_3$, and $R_4$ are hydrogen, alkyl as defined above, fluoro, chloro, bromo, nitro, trifluoromethyl, or alkylthio.

The invention also comprises the pharmacologically acceptable acid addition salts of the compounds of formula 11.

The more desirable compounds are of the formula 11A:

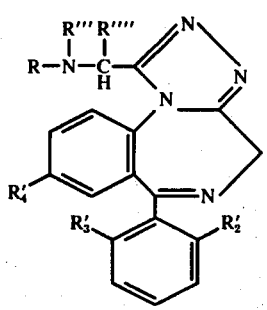

wherein R is cyclopropyl, cyclopropylmethyl, or allyl; R''' and R'''' are hydrogen or methyl; $R'_2$ is hydrogen, chloro, or fluoro; $R'_3$ is hydrogen, or fluoro if $R'_2$ is fluoro; $R'_4$ is hydrogen, fluoro, chloro, bromo, nitro, or trifluoromethyl, and the pharmacologically acceptable salts thereof.

The most desirable compounds of this invention are of the formula 11B:

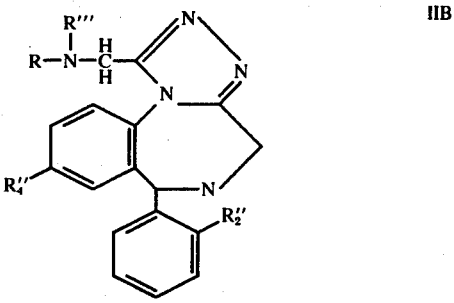

wherein R is cyclopropyl, cyclopropylmethyl or allyl; wherein R''' is hydrogen or methyl; wherein $R''_2$ and $R''_4$ are hydrogen or chloro and the pharmacologically acceptable acid addition salts thereof.

The process of this invention comprises: treating a compound of formula 1 above, in an inert organic solvent at 10 to 100° C. with a secondary amine of the formula

defined as hereinabove. An alkali metal iodide can be used to facilitate the reaction.

DESCRIPTION OF THE PREFERRED EMBODIMENT

Alkyl groups of 1 to 3 carbon atoms, inclusive, are exemplified by methyl, ethyl, propyl, and isopropyl.

The tranquilization activity of the new compounds of formula 11 (including 11A and 11B) and the pharmacologically acceptable acid addition salts thereof were tested in mice as follows:

Chimney test: [Med. Exp. 4, 145 (1961)]: The test determines the ability of mice to back up and out of a vertical glass cylinder within 30 seconds. At the effective dosage 50% of the mice failed doing it.

Dish test: Mice in Petril dishes (10 cm. diameter, 5 cm, high, partially embedded in wood shavings), climb out in a very short time, when not treated. Mice remaining in the dish for more than 3 minutes indicates tranquilization. $ED_{50}$ equals the dose of test compound at which 50% of the mice remain in the dish.

Pedestal test: The untreated mouse leaves the pedestal in less than a minute to climb back to the floor of the standard mouse box. Tranquilized mice will stay on the pedestal for more than 1 minute.

Nicotine antagonism test: Mice in a group of 6 are injected with the test compound. Thirty minutes later the mice including control (untreated) mice are injected with nicotine salicylate (2 mg./kg.). The control mice show over stimulation, i.e., (1) running convulsions followed by (2) tonic extensor fits; followed by (3) death. The effective dosage $ED_{50}$ is that at which 50% of the mice are free of tonic extensor fits and avoid death.

The pharmaceutical forms contemplated by this invention include pharmaceutical compositions suited for oral, parenteral, and rectal use, e.e., tablets, powder packets, cachets, dragees, capsules, solutions, suspensions, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Water or oil, e.g., coconut oil, sesame oil, safflower oil, cottonseed oil, peanut oil may be used for preparing solutions or suspensions of the active drug. Sweetening, coloring and flavoring agents may be added.

For mammals and birds food premixes, with starch, oatmeal, dried fishmeat, fishmeal, flour and the like can be prepared.

As tranquilizers the compounds of formula 11 can be used in unit dosages of 0.03 mg./kg. and preferably 0.3 to 7.5 mg./kg. in oral or injectable preparations, as described above, to alleviate tension and anxiety in mammals, or birds, such as e.g., occurs when animals are in travel. For animals above 10 kg. of weight the lower dosage ranges are adequate.

Other acid addition salts of the compounds of formula 11 can be made such as the fluosilicic acid addition salts which are useful mothproofing compounds or the trichloroacetates useful as herbicides against Johnson grass, Bermuda grass, yellow foxtail and green foxtail, and quack grass.

The starting compounds (1) of this invention and the process of making them are known, e.g. sealed British Specification 1,331,917.

In carrying out the process of this invention a selected starting compound of formula 1 in an inert organic solvent is reacted between 10° to 100° C. with a selected amine

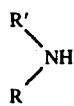

defined as herein above.

As solvents dimethylformamide, dimethylacetamide, diethylacetamide, dimethylsulfoxide, tetrahydrofuran, dioxane, methanol, ethanol or hexamethylphosphoric triamide (HMPT) can be used.

In the preferred embodiment of this invention a nitrogen atmosphere, and an alkali metal iodide e.g. lithium, sodium or potassium iodide as a catalyst is used. The reaction period is from 1 to 24 hours. After termination of the reaction, the product is recovered and purified by conventional procedures, such as extraction, filtration, crystallization, chromatography, and/or the like.

The following preparations and examples are illustrative of the processes and products of this invention, but are not to be construed as limiting.

Preparation 1 —7-Chloro-5-phenyl-3H-1,4-benzodiazepin-2-yl hydrazine

A stirred mixture of 7-chloro-1,3-dihydro-5-phenyl-2H-1,4-benzodiazepine-2-thione (50 g., 0.174 mole) and methanol (1700 ml.) is treated with hydrazine hydrate (34.9 g.) and allowed to remain at ambient temperature for 1 hour 45 minutes. A slow stream of nitrogen is bubbled through the mixture during this period. The resulting solution is concentrated in vacuo at 25°–30° C. The thus obtained residue is mixed with water and extracted with chloroform. The extract is dried over anhydrous potassium carbonate and concentrated under reduced pressure on the rotary evaporator in such a manner that the chloroform is replaced by ethyl acetate. The resulting mixture is crystallized at 4° C. to give 26.6 g. of 7-chloro-5-phenyl-3H-1,4-benzodiazepin-2-yl hydrazine of melting point 184°–186° C. and 3.04 g. of melting point 204°–2110° C. (60%). This compound decomposes on heating in solvents to an unknown product, melting point 261°–262° C. The analytical sample is crystallized from ethyl acetate and has a melting point 217.5°–219° C.

Anal. calcd. for $C_{15}H_{13}ClN_4$: C, 63.27; H, 4.60; Cl, 12.45; N, 19.68. Found: C, 63.30; H, 4.52; Cl, 12.46; N, 18.86.

Preparation 2—8 -Chloro-1-(chloromethyl)-6-phenyl-4H- s-triazolo[4,3-a][1,4]benzodiazepine 7-Chloro-5-phenyl-3H-1,4-benzodiazepin-2-yl hydrazine (14.2 g., 0.05 mole) is added slowly to acetic acid (150 ml.) with external cooling. A solution of chloroacetyl chloride (5.65 g.) in acetic acid (75 ml.) is then added during 10 minutes, and the red solution is stirred at ambient temperature for 1.5 hours treated with sodium acetate (4.1 g.), stirred again for 30 minutes and then refluxed for 3 hours and 15 minutes. This mixture is cooled, poured into ice water and concentrated to a small volume. It is then diluted with water, neutralized with sodium bicarbonate and extracted with chloroform. The extract is dried over anhydrous magnesium sulfate, concentrated and the residue chromatographed on silica gel (1 kg.) with 1% methanol-99% chloroform. The product obtained from the column is crystallized from EtOAc to give: 6.36 g. of 8-chloro-1-(chloromethyl)-6- phenyl-4H-s-triazolo[4,3-a][1,4]benzodiazepine. The analytical sample has a melting point 183°–186.5° C.

Anal. calcd. for $C_{17}H_{12}Cl_2N_4$: C, 59.49; H, 3.53; Cl, 20.66; N, 16.33. Found: C, 59.59; H, 3.31; Cl, 20.21; N, 16.42.

Preparation 3—8-Chloro-1-(α-chloroethyl)-6-phenyl-H- s-triazolo[4,3-a][1,4]benzodiazepine 7-Chloro-5-phenyl-3H-1,4-benzodiazepin-2-yl hydrazine (2.85 g., 0.01 mole) is added, under nitrogen, with cooling and stirring to glacial acetic acid (30 ml.). A solution of 2-chloropropionyl chloride in acetic acid (15 ml.) is then added dropwise, and the resulting red solution is stirred at room temperature for 1.5 hours, treated with sodium acetate (0.82 g., 0.01 mole), stirred for an additional 30 minutes and then refluxed for 2 hours. This mixture is cooled, poured into ice water and concentrated to a small volume. The residual solution is neutralized with sodium bicarbonate and extracted with methylene chloride. The extract is dried over anhydrous magnesium sulfate and concentrated. The residue is chromatographed on silica gel (400 g.) with 1% methanol-99% chloroform. The product thus obtained is crystallized from a small amount of ethyl acetate to give 1.39 g. of 8-chloro-1-(α-chloroethyl)-6-phenyl-4H-s-triazolo- [4,3-a][1,4]benzodiazepine of melting point 153.5°–156.5° C.

Anal. calcd. for $C_{18}H_{14}Cl_2N_4$: C, 60.52; H, 3.95; Cl, 19.85; N, 15.68. Found: C, 60.34; H, 4.07; Cl, 19.81; N, 15.65.

In the manner given in the preceding Preparations, other 1-(haloalkyl)-6-phenyl-4H-s-triazolo[4,3-a][1,4]-benzodiazepines of formula 1 can be synthesized. Representative compounds, include:
8-nitro-1-(chloromethyl)-6-phenyl-4H-s-triazolo[4,3-a]-[1,4]benzodiazepine;
8-(trifluoromethyl)-1-(bromomethyl)-6-phenyl-4H-s-triazolo[4,3-a][1,4]benzodiazepine;
8-chloro-1-(chloromethyl)-6-(o-chlorophenyl)-4H-s-triazolo-[4,3-a][1,4;) benzodiazepine;
8-nitro-1-(bromomethyl)-6-(o-chlorophenyl)-4H-s-triazolo-[4,3-a][1,4]benzodiazepine;
8-(trifluoromethyl)-1-(chloromethyl)-6-(o-chlorophenyl)-4H-s-triazolo[4,3-a][1,4]benzodiazepine;
1-(chloromethyl)-6-phenyl-4H-s-triazolo[4,3-a][1,4]-benzodiazepine;
8-chloro-1-(chloromethyl)-6-(2,6-difluorophenyl)-4H-s-triazolo[4,3-a][1,4]benzodiazepine;
8-bromo1-(bromomethyl)-6-phenyl-4H-s-triazolo[4,3-a][1,4]-benzodiazepine;
8-(methylthio)-1-(bromomethyl)-6-phenyl-4H-s-triazolo-[4,3-a][1,4]benzodiazepine;
1-(chloromethyl)-6-(o-chlorophenyl)-4H-s-triazolo[4,3-a]-[1,4]benzodiazepine;
7-(propylthio)-1-(1-chloropropyl)- 6-phenyl-4H-s-triazolo-[4,3-a][1,4]benzodiazepine;
7-(ethylthio)-1-(chloromethyl)-6-(m-chlorophenyl)-4H-s-triazolo[4,3-a][1,4]benzodiazepine;
8-chloro-1-(1-chloroethyl)-4-methyl-6-(2,6-difluorophenyl)-4H-s-triazolo[4,3-a][1,4]benzodiazepine;
9-bromo-1-(bromomethyl)-6-(p-chlorophenyl)-4H-s-triazolo-[4,3-a][1,4]benzodiazepine;
10-(trifluoromethyl)-1-(chloromethyl)-6-(p-chlorophenyl)-4H-s-triazolo[4,3-a][1,4]benzodiazepine;
8-fluro-1-(chloromethyl)-6-(o-fluorophenyl)-4H-s-triazolo-[4,3-a][1,4]benzodiazepine;
1-(chloromethyl)-6-(o-fluorophenyl)-4H-s-triazolo[4,3-a]-[1,4]benzodiazepine;
9-bromo-1-(bromomethyl)-6-(o-chlorophenyl)-4H-s-triazolo-[4,3-a][1,4]benzodiazepine;
7-bromo-1-(chloromethyl)-6-(o-chlorophenyl)-4H-s-triazolo[4,3-a][1,4]benzodiazepine;
7-(propylthio)-1-(chloromethyl)-6-(o-chlorophenyl)-4H-s-triazolo[4,3-a][1,4]benzodiazepine;
10-fluro-1-(bromomethyl)-6-(o-chlorophenyl)-4H-s-triazolo-[4,3-a][1,4]benzodiazepine;
10-(trifluoromethyl)-1-(bromomethyl)-6-(o-chlorophenyl)-4H-s-trizaolo[4,3-a][1,4]benzodiazepine;
8-(isopropylthio)-1-(chloromethyl)-6-(o-chlorophenyl)-4H-s-triazolo[4,3-a][1,4]benzodiazepine;
9-bromo-1-(chloromethyl)-6-phenyl-4H-s-triazolo[4,3-a][1,4]-benzodiazepine;
7-bromo-1-(bromomethyl)-6-(o-fluorophenyl)-4H-s-triazolo-[4,3-a][1,4]benzodiazepine;
10-fluro-1-(chloromethyl)-6-(m-chlorophenyl)-4H-s-triazolo-[4,3-a][1,4]benzodiazepine;
9-bromo-1-(bromomethyl)-6-(p-fluorophenyl)-4H-s-triazolo-[4,3-a][1,4]benzodiazepine;
7-chloro-1-(bromomethyl)-6-(o-chlorophenyl)-4H-s-triazolo-[4,3-a][1,4]benzodiazepine;
7-fluoro-1-(bromomethyl)-6-(o-chlorophenyl)-4H-s-triazolo-4H-s-triazolo[4,3-a][1,4]benzodiazepine;
9-(propylthio)-1-(chloromethyl)-6-(o-chlorophenyl)-4H-s-triazolo[4,3-a][1,4]benzodiazepine;
7-nitro-1-bromomethyl)-6-(o-chlorophenyl)-4H-s-triazolo-[4,3-a][1,4]benzodiazepine;
7-(ethylthio)-1-(bromomethyl)-6-(o-chlorophenyl)-4H-s-triazolo[4,3-a][1,4]benzodiazepine;
7-nitro-1-(chloromethyl)-6-(o-fluorophenyl)-4H-s-triazolo-[4,3-a][1,4]benzodiazepine;
7-bromo-1-(chloromethyl)-6-(o-chlorophenyl)-4H-s-triazolo-[4,3-a][1,4]benzodiazepine;
10-(trifluoromethyl)-1-(chloromethyl)-6-(o-fluorophenyl)-4H-s-triazolo[4,3-a][1,4]benzodiazepine;
7-ethyl-1-(chloromethyl)-6-(o-chlorophenyl)-4H-s-triazolo-[4,3-a][1,4]benzodiazepine;
9-fluoro-1-(bromomethyl)-6-(o-chlorophenyl)-4H-s-triazolo-[4,3-a][1,4]benzodiazepine;
9-bromo-1-(chloromethyl)-6-(m-chlorophenyl)-4H-s-triazolo-[4,3-a][1,4]benzodiazepine;
7-(propylthio)-1-(chloromethyl)-6-(p-chlorophenyl)-4H-s-triazolo[4,3-a][1,4]benzodiazepine;
9-(ethylthio)-1-(bromomethyl)-6-(o-chlorophenyl)-4H-s-triazolo[4,3-a][1,4]benzodiazepine;
8-propyl-1-(bromomethyl)-6-(o-chlorophenyl)-4H-s-triazolo-[4,3-a][1,4]benzodiazepine;
7-methyl-1-(1-chloro-2-methylpropyl)-6-phenyl-4H-s-triazolo-[4,3-a][1,4]benzodiazepine;
8-chloro-1-(1-chloroethyl)-6-(m-ethylphenyl)-4H-s-triazolo-[4,3-a][1,4]benzodiazepine;
8-isopropyl-1-(chloromethyl)-4-propyl-6-phenyl-4H-s-triazolo[4,3-a][1,4]benzodiazepine;
8-chloro-1-(1-chloropropyl)-4-isopropyl-6-phenyl-4H-s-triazolo[4,3-a][1,4]benzodiazepine;
7-bromo-1-(chloromethyl)-4-ethyl-6-phenyl-4H-s-triazlo-[4,3-a][1,4]benzodiazepine; and the like.

EXAMPLE 1

8-Chloro-1-[ (cyclopropylamino)methyl]-6-phenyl-4H-s-triazolo[4,3-a][1,4]benzodiazepine A stirred mixture of 8-chloro-1-(chloromethyl)-6-phenyl-4H-s-trizolo[4,3-a][1,4]benzodiazepine, (1.37 g., 0.004 mole), potassium iodide (0.67 g., 0.004 mole), cyclopropylamine (0.685 g., 0.012 mole) and tetrahydrofuran (100 ml.) is kept under nitrogen at ambient temperature (25° C.) for 18 hours and concentrated in vacuo. The residue is mixed with water and extracted with methylene chloride. The extract is washed with brine, dried over anhydrous sodium sulfate and concentrated. The residual oil is dissolved in methylene chloride-methanol-chloroform, treated with activated carbon [Darco (G60)] and silica gel and filtered through diatomaceous earth (Celite). The filtrate is concentrated and crystallized from ethyl acetate to give 0.72 g. of 8-chloro-1-[(cyclopropylamino)methyl]-6-phenyl-4H-s-triazolo[4,3-a][1,4]benzodiazepine of melting point 164°–169° C. The analytical sample has a melting point of 165°–171° C.

Anal. calcd. for $C_{20}H_{18}ClN_5$:
C, 66.02; H, 4.99; Cl, 9.74; N, 19.25.
Found: C, 65.77; H, 5.11; Cl, 9.87; N, 19.15.

EXAMPLE 2

8-Chloro-1-[(cyclopropylmethylamino)methyl]-6-phenyl-4H-s-triazolo[4,3-a][1,4]benzodiazepine A stirred mixture of 8-chloro-1-(chloromethyl)-6-phenyl-4H-s-triazolo[4,3-a][1,4]benzodiazepine (1.37g., 0.004 mole), potassium iodide (0.67 g., 0.004 mole), methylcyclopropylamine (0.84 g., 0.012 mole) and tetrahydrofuran (100 ml.) is kept at ambient temperature (25° C.) for 18 hours and concentrated in vacuo. The residue is mixed with water and extracted with methylene chloride. The extract is washed with brine, dried over anhydrous sodium sulfate and concentrated. The residue is crystallized from ethyl acetate-Skellysolve B hexanes to give 0.50 g. of 8-chloro-1-[(cyclopropylmethylamino)methyl]-6-phenyl-4H-s-triazolo[4,3-a][1,4]benzodiazepine of melting point 165°–168° C. The analytical sample has a melting point 165°–169° C.

Anal. calcd. for $C_{21}H_{20}ClN_5$:
C, 66.75; H, 5.33; Cl, 9.38; N, 18.53.
Found: C, 67.08; H, 5.39; Cl, 9.27; N, 18.08.

EXAMPLE 3

8-Chloro-1-[[(cyclopropylmethyl)amino]methyl]-6-phenyl-4H-s-triazolo[4,3-a][1,4]benzodiazepine A stirred solution of potassium hydroxide (3.57 g., 0.06 mole) in methanol (30 ml.) is cooled in an ice bath, under nitrogen, and treated with (cyclopropylemethyl)amine hydrochloride (6.45 g., 0.06 mole). The resulting mixture is kept in the ice bath for 15 minutes, treated with tetrahydrofuran (250 ml.), 8-chloro-1-(chloromethyl)-6-phenyl-4H-s-triazolo[4,3-a][1,4]benzodiazepine (6.86 g., 0.02 mole) and potassium iodide (3.32 g., 0.02 mole) and kept at ambient temperature for 18 hours. The mixture is concentrated and the residue is mixed with water and extracted with methylene chloride. The extract is washed with brine, dried over anhydrous sodium sulfate, and concentrated. The produce is crystallized once from ethyl acetate and once from methylene chloride-ethyl acetate to give 4.68 g., melting point 154°–157° and 2.10 g., melting point 153°–158° of 8-chloro-1-[[(cyclopropylmethyl)-amino]methyl]-6-phenyl-4H -s-triazolo[4,3-a][1,4]benzodiazepine. The analytical sample has a melting point 154°–156° C.

Anal. calcd. for $C_{21}H_{20}ClN_5$:
C, 66.75; H, 5.33; Cl, 9.38; N, 18.53.
Found: C, 66.96; H, 5.65; Cl, 9.39; N, 18.32.

EXAMPLE 4

8-Chloro-1-[(cyclopropylamine)methyl]-6-(o-chlorophenyl)-4H-s-triazolo[4,3-a][1,4]benzodiazepine In the manner given in Example 1, potassium iodide and 8-chloro-1-(chloromethyl)-6-(o-chlorophenyl)-4H-s-triazolo[4,3-a][1,4]benzodiazepine in tetrahydrofuran is treated with cyclopropylamine to give 8-chloro-1-[(cyclopropylamino)methyl]-6-(o-chlorophenyl)-4H-s-triazolo[4,3-a]-[1,4]benzodiazepine.

EXAMPLE 5

8-Chloro-1-[(cyclopropylmethylamino)methyl]-6-(o-chlorophenyl)-4H-s-triazolo[4,3-a][1,4]benzodiazepine In the manner given in Example 2, potassium iodide, 8-chloro-1-(chloromethyl)-6-(o-chlorophenyl)-4H-s-triazolo-[4,3-a][1,4]benzodiazepine in tetrahydrofuran is treated with methylcyclopropylamine to give 8-chloro-1-[(cyclopropylmethylamino)methyl]-6-(o-chlorophenyl)-4H-s-triazolo-[4,3-a][1,4]benzodiazepine.

EXAMPLE 6

8-Chloro-1-[[(cyclopropylmethyl)amino]methyl]-6-(o-chlorophenyl)-4H-s-triazolo[4,3-a][1,4]benzodiazepine In the manner given in Example 3, a solution of potassium hydroxide and (cyclopropylmethyl)amine hydrochloride is treated with a solution of 8-chloro-1-(chloromethyl)-6-(o-chlorophenyl)-4H-s-triazolo[4,3-a][1,4]-benzodiazepine and potassium iodide in tetrahydrofuran to give 8-chloro-1-[[(cyclopropylmethyl)amino]methyl]-6-(o-chlorophenyl)-4H-s-triazolo[4,3-a][1,4]benzodiazepine.

EXAMPLE 7

8-Nitro-1-[(cyclopropylamine)methyl]-6-(o-chlorophenyl)-4H-s-triazolo[4,3-a][1,4]benzodiazepine In the manner given in Example 1, potassium iodide and 8-nitro-1-(chloromethyl)-6-(o-chlorophenyl)-4H-s-triazolo[4,3-a][1,4]benzodiazepine in tetrahydrofuran is treated with cyclopropylamine to give 8-nitro 1-[(cyclopropylamino)methyl]-6-(o-chlorophenyl)-4H-s-triazolo[4,3-a]-[1,4]benzodiazepine.

EXAMPLE 8

8-Nitro-1-[(cyclopropylmethylamino)methyl]-6-(o-chlorophenyl)-4H-s-triazolo[4,3-a][1,4]benzodiazepine In the manner given in Example 2, potassium iodide and 8-nitro-1-(chloromethyl)-6-(o-chlorophenyl)-4H-s-triazolo[4,3-a][1,4]benzodiazepine in tetrahydrofuran are treated with methylcyclopropylamine to give 8-nitro-1-[(cyclopropylmethylamino)methyl]-6-(o-chlorophenyl)-4H-s-triazolo[4,3-]1,4]benzodiazepine.

EXAMPLE 9

8-Nitro-1-[[(cyclopropylmethyl)amino]methyl]-6-(o-chlorophenyl)-4H-s-triazolo[4,3-a][1,4]benzodiazepine In the manner given in Example 3, a solution of potassium hydroxide and (cyclopropylmethyl)amine hydrochloride is treated with a solution of 8-nitro-1-(chloromethyl)-6-(o-chlorophenyl)-4H-s-triazolo[4,3-a][1,4]-benzodiazepine and potassium iodide in tetrahydrofuran to give 8-nitro-1-[[(cyclopropylmethyl)amino]methyl]-6-(o-chlorophenyl)-4H-s-triazolo[4,3-a][1,4]benzodiazepine.

EXAMPLE 10

8-(Trifluoromethyl)-1-[(cyclopropylamino)methyl]-6-(o-chlorophenyl)-4H-s-triazolo[4,3-a][1,4]-benzodiazepine In the manner given in Example 1, potassium iodide and 8-(trifluoromethyl)-1-(chloromethyl)-6-(o-chlorophenyl)-4H-s-triazolo[4,3-a][1,4]benzodiazepine in tetrahydrofuran is treated with cyclopropylamine to give 8-trifluoromethyl-1-(cyclopropylamino)methyl]-6(o-chlorophenyl)-4H-s-triazolo[4,3-a][1,4]benzodiazepine.

EXAMPLE 11

8-(Trifluoromethyl)-1-[(cyclopropylmethylamino)-methyl]-6-(o-chlorophenyl)-4H-s-triazolo[4,3-a][1,4benzodiazepine In the manner given in Example 2, potassium iodide and 8-(trifluoromethyl)-1-(chloromethyl)-6-(o-chlorophenyl)-4H-s-triazolo[4,3-a][1,4]benzodiazepine in tetrahydrofuran is treated with methylcyclopropylamine to give 8-(trifluoromethyl)-1-[(cyclopropylmethylamino)methyl]-6-(o-chlorophenyl)-4H-s-triazolo[4,3-a][1,4]benzodiazepine.

EXAMPLE 12

8-(Trifluoromethyl)-1-[[(cyclopropylmethyl)-amino]methyl]-6-(o-chlorophenyl)-4H-s-triazolo[4,3-a]-[1,4]benzodiazepine In the manner given in Example 3, a solution of potassium hydroxide and (cyclopropylmethyl)amine hydrochloride is treated with a solution of 8-(trifluoromethyl)-1-(chloromethyl)-6-(o-chlorophenyl)-4H-s-triazolo[4,3-a]-[1,4]benzodiazepine and potassium iodide in tetrahydrofuran to give 8-(trifluoromethyl)-1-[[(cyclopropylmethyl)amino]-methyl]-6-(o-chlorophenyl)-4H-s-triazolo[4,3-a]-benzodiazepine.

EXAMPLE 13

8-Fluoro-1-[(cyclopropylamino)methyl]-6-(o-chlorophenyl)-4H-s-triazolo[4,3-a][1,4]benzodiazepine In the manner given in Example 1, potassium iodide and 8-fluoro-1-(chloromethyl)-6-(o-chlorophenyl)-4H-s-triazolo[4,3-a][1,4]benzodiazepine in tetrahydrofuran is treated with cyclopropylamine to give 8-fluoro-1-[(cyclopropylamino)methyl]-6-(o-chlorophenyl)-4H-s-triazolo[4,3-a]-[1,4]benzodiazepine.

EXAMPLE 14

8-Fluoro-1-[(cyclopropylmethylamino)methyl]-6-(o-chlorophenyl)-4H-s-triazolo[4,3-a][1,4]benzodiazepine In the manner given in Example 2, potassium iodide and 8-fluoro-1-(chloromethyl)-6-(o-chlorophenyl)-4H-s-triazolo[4,3-a][1,4]benzodiazepine in tetrahydrofuran is treated with methylcyclopropylamine to give 8-fluoro-1-[(cyclopropylmethylamino)methyl]-6-(o-chlorophenyl)-4H-s-triazolo[4,3-a][1,4]benzodiazepine.

EXAMPLE 15

1-[[(cyclopropylmethyl)amino]methyl]-6-phenyl-4H-s-triazolo[4,3-a][1,4]benzodiazepine In the manner given in Example 3, a solution of potassium hydroxide and (cyclopropylmethyl)amine hydrochloride is treated with a solution of 1-(chloromethyl)-6-phenyl-4H-s-triazolo[4,3-a][1,4]benzodiazepine and potassium iodide in tetrahydrofuran to give 1-[[(cyclopropylmethyl)-amino]methyl]-6-phenyl-4H-s-triazolo[4,3-a][1,4]benzodiazepine.

EXAMPLE 16

8-Chloro-1-[(cyclopropylamino)methyl]-6-(2,6-difluorophenyl)-4H-s-triazolo[4,3-a][1,4]benzodiazepine In the manner given in Example 1, potassium iodide and 8-chloro-1-(chloromethyl)-6-(2,6-difluorophenyl)-4H-s-triazolo[4,3-a][1,4]benzodiazepine in tetrahydrofuran is treated with cyclopropylamine to give 8-chloro-1-[(cyclopropylamino)methyl]-6-(2,6-difluorophenyl)4H-s-triazolo-[4,3-a][1,4]benzodiazepine.

EXAMPLE 17

8-Chloro-1-[(cyclopropylmethylamino)methyl]-6-(2,6-difluorophenyl)-4H-s-triazolo[4,3-a][1,4]benzodiazepine In the manner given in Example 2, potassium iodide and 8-chloro-1-(chloromethyl)-6-(2,6-difluorophenyl)-4H-s-triazolo[4,3-a][1,4]benzodiazepine in tetrahydrofuran is treated with methylcyclopropylamine to give 8-chloro-1-[(cyclopropylmethylamino)methyl]-6-(2,6-difluorophenyl)-4H-s-triazolo[4,3-a][1,4]benzodiazepine.

EXAMPLE 18

8-Chloro-1-[[(cyclopropylmethyl)amino]methyl]-6-(2,6-difluorophenyl)-4H-s-triazolo[4,3-a][1,4]benzodiazepine In the manner given in Example 3, a solution of potassium hydroxide and (cyclopropylmethyl)amine hydrochloride is treated with a solution of 8-chloro-1-(chloromethyl)-6-(2,6-difluorophenyl)-4H-s-triazolo[4,3-a][1,4]-benzodiazepine and potassium iodide in tetrahydrofuran to give 8-chloro-1-[[(cyclopropylmethyl)amino]methyl]-6-(2,6-difluorophenyl)-4H-s-triazolo[4,3-a][1,4]benzodiazepine.

EXAMPLE 19

8-Bromo-1-[(cyclopropylamino)methyl]-6-phenyl-4H-s-triazolo[4,3-a][1,4]benzodiazepine In the manner given in Example 1, potassium iodide and 8-bromo-1-(chloromethyl)-6-phenyl-4H-s-triazolo-[4,3-a][1,4]benzodiazepine in tetrahydrofuran is treated with cyclopropylamine to give 8-bromo-1-[(cyclopropylamino)methyl]-6-phenyl-4H-s-triazolo[4,3-a][1,4]benzodiazepine

EXAMPLE 20

8-Bromo-1-[(cyclopropylethylamino)methyl]-6-phenyl-4H-s-triazolo[4,3-a][1,4]benzodiazepine In the manner given in Example 2, potassium iodide and 8-bromo-1-(chloromethyl)-6-phenyl-4H-s-triazolo[4,3a]-[1,4]benzodiazepine in tetrahydrofuran is treated with ethylcyclopropylamine to give 8-bromo-1-[(cyclopropylethylamino)methyl]-6-phenyl-4H-s-triazolo[4,3-a][1,4]-benzodiazepine.

EXAMPLE 21

8-Bromo-1-[[(cyclopropylmethyl)amino]methyl]-6-phenyl-4H-s-triazolo[4,3-a][1,4]benzodiazepine In the manner given in Example 3, a solution of potassium hydroxide and (cyclopropylmethyl)amine hydrochloride is treated with a solution of 8-bromo-1-(chloromethyl)-6-phenyl-4H-s-triazolo[4,3-a][1,4]benzodiazepine and potassium iodide in etrahydrofuran to give 8-bromo-1-[[(cyclopropylmethyl)amino]methyl]-6-phenyl-4H-s-triazolo[4,3-a][1,4]benzodiazepine.

EXAMPLE 22

8-(Methylthio)-1-[(cyclopropylamino)methyl]-6-phenyl-4H-s-triazolo[4,3-a][1,4]benzodiazepine In the manner given in Example 1, potassium iodide and 8-(methylthio)-1-(chloromethyl)-6-phenyl-4H-s-triazolo-[4,3-a][1,4]benzodiazepine in tetrahydrofuran is treated with cyclopropylamine to give 8-(methylthio)-1-[(cyclopropylamino)methyl]-6-phenyl-4H-s-triazolo[4,3-a][1,4]-benzodiazepine.

EXAMPLE 23

8-(Methylthio-1-[(cyclopropylpropylamino)-methyl]-6-phenyl-4H-s-triazolo[4,3a][1,4]benzodiazepine In the manner given in Example 2, potassium iodide and 8-(methylthio)-1-(chloromethyl)-6-phenyl-4H-s-triazolo-[4,3-a][1,4]benzodiazepine in tetrahydrofuran is treated with propylcyclopropylamine to give 8-(methylthio)-1-[(cyclopropylpropylamino)methyl]-6-phenyl-4H-s-triazolo-[4,3-a][1,4]benzodiazepine.

EXAMPLE 24

8-(Methylthio)-1-[[(cyclopropylmethyl)amino]methyl]-6-phenyl-4H-s-triazolo[4,3-a][1,4]benzodiazepine In the manner given in Example 3, a solution of potassium hydroxide and (cyclopropylmethyl)amine hydrochloride is treated with a solution of 8-(methylthio)-1-(chloromethyl)-6-phenyl-4H-s-triazlo[4,3-a][1,4]benzodiazepine and potassium iodide in tetrahydrofuran to give 8-(methylthio)-1-[[(cyclopropylmethyl)amino]methyl]-6-phenyl-4H-s-triazolo[4,3-a][1,4benzodiazepine.

EXAMPLE 25

1-[(cyclopropylamino)methyl]-6-(o-chlorophenyl)-4H-s-triazolo[4,3-a][1,4]benzodiazepine In the manner given in Example 1, potassium iodide and 1-(chloromethyl)-6-(o-chlorophenyl)-4H-s-triazolo-[4,3-a][1,4]benzodiazepine in tetrahydrofuran is treated with cyclopropylamine to give 1-[(cyclopropylamino)-methyl]-6-(o-chlorophenyl)-4H-s-triazolo[4,3-a][1,4]-benzodiazepine.

EXAMPLE 26

1-[(cyclopropylmethylamino)methyl]-6-(o-chlorophenyl)-4H-s-triazolo[4,3-a[4,3-][1,4]benzodiazepine In the manner given in Example 2, potassium iodide and 1-(chloromethyl)-6-(o-chlorophenyl)-4H-s-triazolo-[4,3-a][1,4]benzodiazepine in tetrahydrofuran is treated with methylcyclopropylamine to give 1-[(cyclopropylmethylamino)methyl]-6-(o-chlorophenyl)-4H-s-triazolo[4,3-a][1,4]-benzodiazepine.

EXAMPLE 27

1-[[(cyclopropylmethyl)amino]methyl]-6-(o-chlorophenyl)-4H-s-triazolo[4,3-a][1,4]benzodiazepine In the manner given in Example 3, a solution of potassium hydroxide and (cyclopropylmethyl)amine hydrochloride is treated with a solution of 1-(chloromethyl)-6-(o-chlorophenyl)-4-H-s-triazolo[4,3-a][1,4]benzodiazepine and potassium iodide in tetrahydrofuran to give 1-[[(cyclopropylmethyl)amino]methyl]-6-(o-chlorophenyl)-4H-s-triazolo[4,3-a][1,4]benzodiazepine.

EXAMPLE 28

7-(Ethylthio)-1-[(cyclopropylamino)methyl]-6-(m-chlorophenyl)-4H-s-triazolo[4,3-a][1,4]benzodiazepine In the manner given in Example 1, a potassium iodide and 7-(ethylthio)-1-(chloromethyl)-6-(m-chlorophenyl)-4H-s-triazolo[4,3-a][1,4]benzodiazepine in tetrahydrofuran is treated with cyclopropylamine to give 7-(ethylthio)-1-[(cyclopropylamino)methyl]-6-(m-chlorophenyl)-4H-s-triazolo[4,3-a][1,4]benzodiazepine.

EXAMPLE 29

7-(Ethylthio)-1-[(cyclopropylmethylamino)methyl]-6-(m-chlorophenyl)-4H-s-triazolo[4,3-a][1,4]-benzodiazepine In the manner given in Example 2, potassium iodide and 7-(ethylthio)-1-(chloromethyl)-6-(m-chlorophenyl)-4H-s-triazolo[4,3-a][1,4]benzodiazepine in tetrahydrofuran is treated with methylcyclopropylamine to give 7-(ethylthio)-1-[(cyclopropylmethylamino)methyl]-6-(m-chlorophenyl)-4H-s-triazolo[4,3-a][1,4]benzodiazepine.

EXAMPLE 30

7-(Ethylthio)-1-[[(cyclopropylmethyl)amino]methyl]-6-(m-chlorophenyl)-4H-s-triazolo[4,3-a][1,4]-benzodiazepine In the manner given in Example 3, a solution of potassium hydroxide and (cyclopropylmethyl)amine hydrochloride is treated with a solution of 7-(ethylthio)-1-(chloromethyl)-6-(m-chlorophenyl)-4H-s-triazolo[4,3-a][1,4]benzodiazepine in tetrahydrofuran to give 7-(ethylthio)-1-[[(cyclopropylmethyl)amino]methyl]-6-(m-chlorophenyl)-4H-s-triazolo-[4,3-a][1,4]benzodiazepine.

EXAMPLE 31

8-Chloro-1-[(allylamino)methyl]-6-phenyl 4H-s-triazolo[4,3-][1,4]benzodiazepine

A stirred mixture of 8-chloro-1-(chloromethyl)-6-phenyl-4H-s-triazolo[4,3-a][1,4]benzodiazepine (1.37 g., 0.004 mole), potassium iodide (0.67 g., 0.004 mole), allylamine (0.685 g., 0.012 mole) and tetrahydrofuran (100 ml.) is kept at ambient temperature (25° C.) for 18 hours and concentrated in vacuo. The residue is mixed with water and extracted with methylene chloride. The extract is washed with brine, dried over anhydrous sodium sulfate and concentrated. The residue is crystallized once from ethyl acetate-Skellysolve B hexanes and then from methylene chloride-ethyl acetate-Skellysolve B hexanes to give 0.495 g., of 8-chloro-1-[(allylamino)-methyl]-6-phenyl-4H-s-triazolo[4,3-a][1,4]benzodiazepine of melting point 127°–129° C. The analytical sample has a melting point 128°–132° C.

Anal. calcd. for $C_{20}H_{18}ClN_5$:
C, 66.02; H, 4.99; Cl, 9.74; N, 19.25.
Found: C, 66.09; H, 5.12; Cl, 9.63; N, 19.19.

EXAMPLE 32

8-Chloro-1-[(allylmethylamino)methyl]-6-phenyl-4H-s-triazolo[4,3-a][1,4]benzodiazepine A stirred mixture of 8-chloro-1-(chloromethyl)-6-phenyl-4-H-s-triazolo[4,3-][1,4]benzodiazepine (1.37 g., 0.004 mole), potassium iodide (0.67 g., 0.004 mole), methylamine (0.84 g., 0.012 mole) and tetrahydrofuran (100 ml.) is kept at ambient temperature (25° C.) for 18 hours and concentrated in vacuo. The residue is mixed with water and extracted with methylene chloride. The extract is washed with brine, dried over anhydrous sodium sulfate and concentrated. The residue is crystallized from ethyl aceate-Skellysolve B hexanes to give 1.19 g. of 8-chloro-1-[(allylmethylamino)-methyl]-6-phenyl-4H-s-triazolo[4,3-a][1,4]benzodiazepine of melting point 157°–160° C. The analytical sample has a melting point of 158°–164° C.

Anal. calcd. for $C_{21}H_{20}ClN_5$:
C, 66.75; H, 5.33; Cl, 9.38; N, 18.53.
Found: C, 66.87; H, 5.46; Cl, 9.42; N, 18.67.

EXAMPLE 33

8-Chloro-1-[(allylamino)methyl]-6-(o-chlorophenyl)-4H-s-triazolo[4,3-a][1,4]benzodiazepine In the manner given in Example 31, 8-chloro-1-(chloromethyl)-6-(o-chlorophenyl)-4H-s-triazolo[4,3- a][1,4]benzodiazepine, potassium iodide and allylamine in tetrahydrofuran are reacted to give 8-chloro-1-[(allylamino)methyl-6-(o-chlorophenyl)-4H-s-triazolo[4,3-a][1,4]benzodiazepine.

EXAMPLE 34

8-Chloro-1-[(allylmethylamino)methyl]-6-(o-chlorophenyl)-4H-s-triazolo[4,3-a][1,4]benzodiazepine In the manner given in Example 32, 8-chloro-1-(chloromethyl)-6-(o-chlorophenyl)-4H-s-triazolo[4,3-a][1,4]benzodiazepine, potassium iodide, and methylallylamine in tetrahydrofuran are reacted to give 8-chloro-1-[(allylmethylamino)methyl]-6-(o-chlorophenyl)-4H-s-triazolo[4,3-a]-[1,4]benzodiazepine.

EXAMPLE 35

8-Nitro-1-[(allylamino)methyl]-6-(o-chlorophenyl)-4H-s-triazolo[4,3][1,4]enzodiazepine In the manner given in Example 31, 8-nitro-1-(chloromethyl)-6-(o-chlorophenyl)-4H-s-triazolo[4,3-a][1,4]benzodiazenine, potassium iodide and allylamine in tetrahydrofuran is reacted to give 8-nitro-1-[(allylamino)methyl]-6-(o-chlorophenyl)-4H-s-triazolo[4,3-a][1,4]benzodiazepine.

EXAMPLE 36

8-Nitro-1-[(allylmethylamino)methyl]-6-(o-chlorophenyl)-4H-s-triazolo[4,3-a][1,4]benzodiazepine In the manner given in Example 32, 8-nitro-1-(chloromethyl(-6-(o-chlorophenyl)-4H-s-triazolo[4,3-a][1,4]-benzodiazepine, potassium iodide, and methylallylamine in tetrahydrofuran are reacted to give 8-nitro-1-[(allyl-methylamino)methyl]-6-(o-chlorophenyl)-4H-s-triazolo-[4,3-a][1,4]benzodiazepine.

EXAMPLE 37

81-(Trifluormethyl)-1-[(allylamino)methyl]-6-(o-chlorophenyl)-4H-s-triazolo[4,3-a][1,4]benzodiazepine In the manner given in Example 31, 8-(trifluoromethyl)-1-(chloromethyl)-6-(o-chlorophenyl)-4H-s-triazolo[4,3-a]-[1,4]benzodiazepine, potassium iodide and allylamine in tetrahydrofuran are reacted to give 8-(trifluoromethyl)-1-(allylamino)methyl]-6-(o-chlorophenyl)-4H-s-triazolo[4,3-a]-[1,4]benzodiazepine.

EXAMPLE 38

8-(Trifluoromethyl)-1-[(allylmethylamino)-methyl]-6-(o-chlorophenyl)-4H-s-triazolo[4,3-a][1,4]benzodiazepine In the manner given in Example 32, 8-(trifluoromethyl)-1-(chloromethyl)-6-(o-chlorophenyl)-4H-s-triazolo[4,3-a]-[1,4]benzodiazepine, potassium iodide, and methylallylamine in tetrahydrofuran are reacted to give 8-(trifluoromethyl)-1-[(allylmethylamino)methyl]-6-(o-chlorophenyl)-4H-s-triazolo[4,3-a][1,4]benzodiazepine.

EXAMPLE 39

8-Fluoro-1-[(allylamino)methyl]-6-(o-chlorophenyl)-4H-s-triazolo[4,3-a][1,4]benzodiazepine In the manner given in Example 31, 8-fluoro-1-(chloromethyl)-6-(o-chlorophenyl)-4H-s-triazolo[4,3-a]-[1,4]benzodiazepine, potassium iodide and allylamine in tetrahydrofuran are reacted to give 8-fluoro-1-[(allyl-amino)methyl]-6-(o-chlorophenyl)-4H-s-triazolo[4,3-a]-[1,4]benzodiazepine.

EXAMPLE 40

8-Fluoro-1-[(allylmethylamino)methyl]-6-(o-chlorophenyl)-4H-s-triazolo[4,3-a][1,4]benzodiazepine In the manner given in Example 32, 8-fluoro-1-(chloromethyl)-6-(o-chlorophenyl)-4H-s-triazolo[4,3-a][1,4]benzodiazepine, potassium iodide, and methylallylamine in tetrahydrofuran are reacted to give 8-fluoro-1-[(allylmethylamino)methyl]-6-(o-chlorophenyl)-4H-s-triazolo-[4,3-a][1,4]benzodiazepine.

EXAMPLE 41

8-Chloro-1-[(allylamino)methyl]-6-(2,6-difluorophenyl)-4H-s-triazolo[4,3-a][1,4]benzoidiazepine In the manner given in Example 31, 8-chloro-1-(chloromethyl)-6-(2,6-difluorophenyl)-4H-s-triazolo[4,3-a][1,4]-benzodiazepine, potassium iodide and allylamine in tetrahydrofuran are reacted to give 8-chloro-1-[(allylamino)-methyl]-6-(2,6-difluorophenyl)-4H-s-triazolo[4,3-a][1,4]-benzodiazepine.

EXAMPLE 42

8-Chloro-1-[(allylmethylamino)methyl]-6-(2,6-difluorophenyl)-4H-s-triazolo[4,3-a[]1,4]benzodiazepine In the manner given in Example 32, 8-chloro-1-(chloromethyl)-6-(2,6-difluorophenyl)-4-H-s-triazolo[4,3-][1,4]-benzodiazepine, potassium iodide, and methylallylamine in tetrahydrofuran are reacted to give 8-chloro-1-[(allylmethylamino)methyl]-6-(2,6-difluorophenyl)-4H-s-triazolo-[1,3-a][1,4]benzodiazepine.

EXAMPLE 43

8-Bromo-1-[(allylamino)methyl]-6-phenyl-4-H-s-triazolo[4,3-a][1,4]benzodiazepine In the manner given in Example 31, 8-bromo-1-(chloromethyl) -6-phenyl-4H-s-triazolo[4,3-a]benzodiazepine, potassium iodide and allylamine in tetrahydrofuran are reacted to give 8-bromo-1-[(allylamino)methyl]-6-phenyl-4H-s-triazolo[4,3-a][1,4]benzodiazepine.

EXAMPLE 44

8-Bromo-1-[(allylmethylamino)methyl]-6-phenyl-4-H-s-triazolo[4,3-a][1,4]benzodiazepine In the manner given in Example 32, 8-bromo-1-(chloromethyl)-6-phenyl-4H-s-triazolo[4,3-a][1,4]benzodiazepine, potassium iodide, and methylallylamine in tetrahydrofuran are reacted to give 8-bromo-1-[(allylmethylamino)methyl]-6-phenyl-4H-s-triazolo[4,3-a][1,4]benzodiazepine.

EXAMPLE 45

8-(Methylthio)-1-[(allylamino)methyl]-6-phenyl-4H-s-triazolo[4,3-a[]1,4]benzodiazepine In the manner given in Example 31, 8-(methylthio)-1-(chloromethyl)-6-phenyl-4H-s-triazolo[4,3-a][1,4]benzodiazepine, potassium iodide and allylamine in tetrahydrofuran are reacted to give 8-(methylthio)-1-[(allylamino)-methyl]-6-phenyl-4H-s-triazolo[4,3-a][1,4]benzodiazepine.

EXAMPLE 46

8-(Methylthio)-1-[(allylmethylamino)methyl]-6-phenyl-4H-s-triazolo][1,4]benzodiazepine In the manner given in Example 32, 8-(methylthio)-1-(chloromethyl)-6-phenyl-4H-s-triazolo[4,3-a][1,4]benzodiazepine, potassium iodide, and methylallylamine in tetrahydrofuran are reacted to give 8-(methylthio)-1-[(allylmethylamino)methyl]-6-phenyl-4H-s-triazolo[4,3-a][1,4]-benzodiazepine.

EXAMPLE 47

1-[(allylamino)methyl]-6-(o-chlorophenyl)-4H-s-triazolo[4,3-a][1,4]benzodiazepine In the manner given in Example 31, 1-(chloromethyl)-6-(o-chlorophenyl)-4H-s-triazolo[4,3-a][1,4]benzodiazepine, potassium iodide and allylamine in tetrahydrofuran are reacted to give 1-[(allylamino)methyl]-6-(o-chlorophenyl)-4H-s-triazolo[4,3-a][1,4]benzodiazepine.

EXAMPLE 48

1-[(allylmethylamino)methyl]-6-(o-chlorophenyl)-4H-s-triazolo[4,3-a][1,4]benzodiazepine In the manner given in Example 32, 1-(chloromethyl)-6-(o-chlorophenyl)-4H-s-triazolo[4,3-a][1,4]benzodiazepine, potassium iodide, and methylallylamine in tetrahydrofuran are reacted to give 1-[(allylmethylamino)methyl]-6-chlorophenyl)-4H-s-triazolo[4,3-a][1,4]benzodiazepine.

EXAMPLE 49

7-(Ethylthio-1-[(allylamino)methyl]-6-(m-chlorophenyl)-4H-s-triazolo[4,3-a][1,4]benzodiazepine In the manner given in Example 32, 7-(ethylthio)-1-(chloromethyl)-6-(m-chlorophenyl)-4H-s-triazolo[4,3-a]-[1,4]benzodiazepine, potassium iodide and allylamine in tetrahydrofuran are reacted to give 7-(ethylthio)-1-[(allylamino)methyl]-6-(m-chlorophenyl)-4H-s-triazolo[4,3-a][1,4]-benzodiazepine.

EXAMPLE 50

7-(Ethylthio)-1-[(allylpropylamino)methyl]-6-(m-chlorophenyl)-4H-s-triazolo[4,3-a][1,4]benzodiazepine In the manner given in Example 32, 7-(ethylthio)-1-(chloromethyl)-6-(m-chlorophenyl)-4H-s-triazolo[4,3-a]-[1,4]benzodiazepine, potassium iodide and propylallylamine in tetrahydrofuran are reacted to give 7-(ethylthio)-1-[(allylpropylamino)methyl]-6-(m-chlorophenyl)-4H-s-triazolo-[4,3-a][1,4]benzodiazepine.

EXAMPLE 51

8-Chloro-1-[[(cyclopropylmethyl)methylamino]methyl]-6-phenyl-4H-s-triazolo[4,3-a][1,4]benzodiazepine In the manner given in Example 2, potassium iodide and 3-chloro-1-(chloromethyl)-6-phenyl-4H-s-triazolo- [4,3-a][1,4]benzodiazepine in tetrahydrofuran are treated with methyl(cyclopropylmethyl)amine to give 8-chloro-1-[[(cyclopropylmethyl)methylamino]methyl]-6-phenyl-4H-s-triazolo[4,3-a][1,4]benzodiazepine.

EXAMPLE 52

8-Chloro-1-[[(cyclopropylmethyl)methylamino]methyl]-6-(o-chlorophenyl)-4H-s-triazolo[4,3-a][1,4]-benzodiazepine In the manner given in Example 2, potassium iodide and 8-chloro-1-(chloromethyl)-6-(o-chlorophenyl)-4H-s-triazolo[4,3-a][1,4]benzodiazepine in tetrahydrofuran are treated with methyl(cyclopropylmethyl)amine to give 8-chloro-1-[[(cyclopropylmethyl)methylamino]methyl]-6-(o-chlorophenyl)-4H-s-triazolo[4,3-a][1,4]benzodiazepine.

EXAMPLE 53

8-Chloro-1-[[(cyclopropylmethyl)methylamino]-methyl]-6-phenyl-4H-s-triazolo[4,3-a][1,4]benzodiazepine A stirred mixture of 8-chloro-1-[[(cyclopropylmethyl)-amino]methyl]-6-phenyl-4H-s-triazolo[4,3-a][1,4]benzodiazepine (1.89 g., 0.005 mole) and acetonitrile (30 ml.), under nitrogen is treated successively with 37% aqueous formaldehyde (1 ml.) and sodium cyanoborohydride (0.25 g., 0.004 mole). To this mixture is slowly added during 1 hour a solution of acetic acid (0.15 ml.) in acetonitrile (5 ml.). The resulting mixture is kept at ambient temperature for 2 hours and concentrated in vacuo. The residue is mixed with a solution of 25% aqueous ethylenediamine (25 ml.) and methanol (50 ml.) and refluxed, under nitrogen for 0.5 hours. The cooled mixture is mixed with water, treated with a little sodium chloride and extracted with methylene chloride. The extract is washed with brine, dried over anhydrous sodium sulfate and concentrated. The residue is chromatographed on silica gel (100 g.) with 2.5% methanol-97.5% chloroform. The product thus obtained is crystallized from ethyl acetate and methylene chloride-ethyl acetate to give 1.07 g. of 8-chloro-1-[[(cyclopropylmethyl)methylamino]methyl]-6-phenyl-4H-s-triazolo[4,3-a]-[1,4]benzodiazepine of melting point 171°–176° C. and 0.135 g. of melting point 171.5°–174.5° C.

Anal. calcd. for $C_{22}H_{22}ClN_5$:
C, 67.43; H, 5.66; Cl, 9.05; N, 17.87.
Found: C, 67.55; H, 5.80; Cl, 9.21; N, 17.58.

In the manner given in the preceding examples other 1-substituted-6-phenyl-4H-s-triazolobenzodiazepines of formula ll can be synthesized. Representative compounds, thus obtained, include:

8-nitro-1-[(cyclopropylamino)methyl]-6-phenyl-4-H-s-triazolo[4,3-a][1,4]benzodiazepine;
8-(trifluoromethyl)-1-[(cyclopropylamino)methyl]-6-phenyl-4H-s-triazolo[4,3-a][1,4]benzodiazepine;
8-chloro-1-[)cyclopropylamino)methyl]-6-(2,6-difluorophenyl)-4-methyl-4H-s-triazolo[4,3-a][1,4]benzodiazepine:
9-bromo-1-[(cyclopropylamino)methyl]-6-(p-chlorophenyl)-4H-s-triazolo[4,3-a][1,4]benzodiazepine;
10-(trifluromethyl)-1-[(cyclopropylamino)methyl]-6-p-chlorophenyl)-4H-s-triazolo[4,3-a][1,4]benzodiazepine;
7-fluoro-1-[(cyclopropylamino)methyl]-6-(o-chlorophenyl)-4H-s-triazolo[4,3-a][1,4]benzodiazepine;
8-fluror-1-[(cylcopropylamino)methyl]-6-(o-fluorophenyl)-4H-s-triazolo[4,3-a][1,4]benzodiazepine;
1-[(cyclopropylamino)methyl]-6-(o-fluorophenyl)-4H-s-triazolo[4,3-a][1,4]benzodiazepine;
9-bromo-1-[(cyclopropylmethylamino)methyl]-6-(o-chlorophenyl)-4H-s-triazolo[4,3-a][1,4]benzodiazepine;
7-bromo-1-[(cyclopropylmethylamino)methyl]-6-(o-chlorophenyl)-4H-s-triazolo[4,3-a][1,4]benzodiazepine;
7-(propylthio)-1-[(cyclopropylmethylamino)methyl]-6-(o-chlorophenyl)-4H-s-triazolo[4,3-a][1,4]benzodiazepine;

10-fluoro-1-[(cyclopropylmethylamino)methyl]-6-(o-chlorophenyl)-4H-s-triazolo[4,3-a][1,4]benzodiazepine;
10-(trifluoromethyl)-1-[(cyclopropylmethylaino)methyl]-6-(o-chlorophenyl)-4H-s-triazolo[4,3-a][1,4]benzodiazepine;
8-(isopropylthio)-1-[(cyclopropylmethylamino)methyl]-6-(o-chlorophenyl)-4H-s-triazolo[4,3-a][1,4]benzodiazepine;
9-bromo-1-[(cyclopropylmethyl)amino]methyl]-6-phenyl-4H-s-triazolo[4,3-a][1,4]benzodiazepine;
7-bromo-1-[[(cyclopropylmethyl)amino[methyl]-6-(o-fluorophenyl)-4H-s-triazolo[4,3-a][1,4]benzodiazepine;
7-(propylthio)-1-[[(cyclopropylmethyl)amino]methyl]-6-(o-chlorophenyl)-4H-s-triazolo[4,5-a][1,4]benzodiazepine;
1-[[(cyclopropylmethyl)methylamino]methyl]-6-phenyl-4H-s-triazolo[4,3-a][1,4]benzodiazepine;
1-[[(cyclopropylmethyl)methylamino]methyl]-6-(o-chlorophenyl)-4H-s-triazolo[4,3-a][1,4]benzodiacepine;
8-nitro-1-[[(cyclopropylmethyl)methyl)methylamino]methyl]-6-(o-chlorophenyl)-4H-s-triazolo[4,3-a][1,4]benzodiazepine;
8-nitro-1-[[(cyclopropylmethyl)methyl)methylamino]methyl]-6-phenyl-4H-s-triazolo[4,3-a][1,4benzodiazepine;
10-fluoro-1-[[(cyclopropylmethyl)amino]methyl]-6-(m-chlorophenyl)-4H-s-triazolo[4,3-a][1,4]benzodiazepine;
9-bromo-1-[[(cyclopropylmethyl)amino]methyl]-6-(p-fluorophenyl)-4H-s-triazolo[4,3-a][1,4]benzodiazepine; 9-bromo-1-[(allylamino)methyl]-6-(o-chlorophenyl)-4H-s-triazolo[4,3-a][1,4]benzodiazepine;
10-fluoro-1-[(allylamino)methyl]-6-(o-chlorophenyl)-4H-s-triazolo[4,3-a][1,4]benzodiazepine;
7-fluoro-1-[)allylamino)methyl]-6-(o-chlorophenyl)-4H-s-triazolo[4,3-a][1,4]benzodiazepine;
7-bromo-1-[(allylamino)methyl]-6-(o-chlorophenyl)-4H-s-triazolo[4,1]benzodiazepine;
7-chloro-1-[(allylamino)methyl]-6-(o-chlorophenyl)-4H-s-triazolo[4,3-a][1,4]benzodiazepine;
7-(ethylthio)-1-[(allylamino)methyl]-6-(o-chlorophenyl)-4H-s-triazolo[4,3-a][1,4]benzodiazepine;
9-(propylthio)-1-[(allylamino)methyl]-6-(o-chlorophenyl)-4H-s-triazolo[4,3-a][1,4]benzodiazepine;
10-(trifluoromethyl)-1-[(allylamino)methyl]-6-)o-chlorophenyl)-4H-s-triazolo[4,3-a][1,4]benzodiazepine;
7-nitro-1-[(allylamino)methyl]-6-(o-chlorophenyl)-4Hs-triazolo[4,3-a][1,4]benzodiazepine;
7-nitro-1-[(allylmethylamino)methyl]-6-(o-fluorophenyl)-4H-s-triazolo[4,3-a][1,4]benzodiazepine;
9-bromo-1-[(alklylmethylamino)methyl]-6-(o-chlorophenyl)-4H-s-triazolo[4,3-a][1,4]benzodiazepine;
7-bromo-1-[(allylmethylamino)methyl]-6-(o-chlorophenyl)-4H-s-triazolo[4,3-a]1,4]benzodiazepine;
10-(trifluoromethyl)-1-[(allylmethylamino)methyl]-6-(o-chlorophenyl)-4H-s-triazolo[4,3-a][1,4]benzodiazepine;
7-chloro-1-[(allylmethylamino)methyl]-6-(o-chlorophenyl)-4H-s-triazolo[4,3-a][1,4]benzodiazepine;
7-fluoro-1-[(allylmethylamino)methyl]-6-(O-chlorophenyl)-4H-s-triazolo[4,3-a][1,4]benzodiazepine;
7-(ethylthio)-1-[(allymethylamino)methyl[-6-(0-chlorphenyl)-4H-s-triazolo[4,3-a][1,4]benzodiazepine;
7-nitro-1-[(allylethylamino)methyl]-6-(o-fluorophenyl)-4H-s-triazolo[4,3-a][1,4]benzodiazepine;
9-bromo-1-[(allylethylamino)methyl]-6-(o-chlorophenyl)-4H-s-triaolo[4,3-a][1,4]benzodiazepine;
7-bromo-1-[(allylethylamino)methyl]-6-(o-chlorophenyl)-4h-s-triazolo[4,3-a][1,4]benzodiazepine;
10-(trifluoromethyl)-1-[(allylpropylamino)methyl]-6-(os-chlorophenyl)-4H-s-triazolo[4,3-a][1,4]benzodiazepine;
7-chloro-1-[(allylpropylamino)methyl]-6-(o-chlorophenyl)-4H-s-triazolo[1,4]benzodiazepine;
7-fluoro-1-[(alylpropylamino)methyl]-6-(o-chlorophenyl)-4H-s-triazolo[1,4]benzodiazepine;
7-(ethylthio)-1-[(allylpropylamino)methyl]-6-(o-chlorophenyl)-4H-s-triazolo[4,3-a][1,4]benzodiazepine;
9-fluoro-1-[(allylisopropylamino)methyl]-6-(o-chlorophenyl)-4H-s-triazolo[4,3-a][1,4]benzodiazepine;
9-bromo-1-[(allylmethylamino)methyl]-6-(m-chlorophenyl)-4H-s-triazolo[4,3-a][1,4]benzodiazepine;
7-(propylthio)-1-[(allylmethylamino)methyl]-6-(p-chlorophenyl)-4H-s-triazolo[4,3-a][1,4]benzodiazepine;
10-(trifluoromethyl)-1-[(allylmethylamino)methyl]-6-(o-fluorophenyl)-4H-s-triazolo[4,3-a][1,4]benzodiazepine;
9-(ethylthio)-1-[(allylmethlyamino)methyl]-6-(o-chlorophenyl)-4H-s-triazolo[4,3-a][1,4]benzodiazepine;
7-(ethylthio)-1-[(allylmethylamino)methyl]-6-(o-chlorophenyl)-4H-s-triazolo[4,3-a][1,4]benzodiazepine;
7-ethyl-1-[(cyclopropylamino)methyl]-6-(o-chlorophenyl)-4H-s-triazolo[4,3-a][1,4]benzodiazepine;
8-propyl-1-[(cyclopropylmethylamino)methyl]-6-(o-chlorophenyl)-4H-s-triazolo[4,3-a][1,4]benzodiazepine;
7-methyl-1-[(cyclopropylmethyl)amino]-2-methylpropyl]-6-phenyl-4h-s-triazolo[4,3-a][1,4]benzodiazepine;
8-chloro-1-[(allylmaino)methyl[6-(m-ethylphenyl)-4H-s-triazolo[4,3-a][1,4]benzodiazepine;
8-choloro-1-[1-(cyclopropylamino)propyl]-4-isopropyl-6-phenyl-4H-s-triazolo[4,3-a][1,4]benzodiazepine;
7-bromo-1-[(allylmethylamino)methyl[-4-ethyl-6-phenyl-4H-s-triazolo[4,3-a][1,4]benzodiazepine; and the like.

The novel compounds of fourmula 11 can be reacted with selected acids e.g. hydrochloric, hydrobromic, sulfuric, phosphoric, tartaric, citric, lactic, cyclohexanesulfamic, toluenesulfonic, methanesulfonic, and other acids to give the corresponding pharmaceutically acceptable acid addition salts. This reaction is carried out under conventional conditions, in solvents such as either, dioxane, tetrahydrofuran, andthe like at room temperatures, and the resulting precipitated salts are collected by filtration. These salts can be used in place of the free base for the same pharmaceutical purpose described before.

I claim:
1. 8-Chloro-1-[(allylamino)methyl]-6-phenyl-4H-s-triazolo[4,3a][1,4]benzodiazepine.
2. 8-Chloro-1-[(allylamino)methyl]-6-(o-chlorophenyl)-4H-s-triazolo[4,3-a][1,4]benzodiazepine.

3. [(allylaminino)methyl]-6-(o-chlorophenyl]-4H-s-triazolo[4,3-a][1,4]benzodiazepine.

4. 8-chloro-[N-allyl-N-methylamine)methyl]-6-phenyl-4H-s-triazolo[4,3-a][1,4]benzodiazepine.

5. 8-Chloro-1-[(N-allyl-N-methylamino)methyl]-6-(o-chlorophenyl]-4H-s-triazolo[4,3-a][1,4]benzodiazepine.

6. 1-[N-allyl-N-methylamine)methyl]-6-(o-chlorophenyl)-4H-s-triazolo[4,3-a][1,4]benzodiazepine.

* * * * *

UNITED STATES PATENT AND TRADEMARK OFFICE
CERTIFICATE OF CORRECTION

PATENT NO. : 4,021,441
DATED : May 3, 1977
INVENTOR(S) : Jackson B. Hester, Jr.

It is certified that error appears in the above-identified patent and that said Letters Patent are hereby corrected as shown below:

Column 19, line 1: "[(allyl" should read -- 1-[(allyl --
line 3: "8-chloro-[N-allyl" should read -- 8-chloro-1-[(N-allyl --
line 3: "methylamine" should read -- methylamino --
Column 20, line 3: "1-[N-allyl-N-methylamine)" should read -- 1-[(N-allyl-N-methylamino) --

Signed and Sealed this

Thirty-first Day of July 1979

[SEAL]

Attest:

Attesting Officer

LUTRELLE F. PARKER
Acting Commissioner of Patents and Trademarks